United States Patent
Riddick et al.

(10) Patent No.: US 11,879,794 B2
(45) Date of Patent: Jan. 23, 2024

(54) COMPRESSION APPARATUS FOR AUTOMATING SPECIMEN TESTING

(71) Applicant: Illinois Tool Works Inc., Glenview, IL (US)

(72) Inventors: Adrian Riddick, Norwood, MA (US); Daniel Chouinard, Norwood, MA (US); Brian Salem, Norwood, MA (US); Christopher Hines, Norwood, MA (US)

(73) Assignee: Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 17/578,772

(22) Filed: Jan. 19, 2022

(65) Prior Publication Data
US 2022/0228933 A1    Jul. 21, 2022

Related U.S. Application Data

(60) Provisional application No. 63/140,061, filed on Jan. 21, 2021.

(51) Int. Cl.
*G01L 1/22* (2006.01)

(52) U.S. Cl.
CPC .......... *G01L 1/2287* (2013.01); *G01L 1/2218* (2013.01)

(58) Field of Classification Search
None
See application file for complete search history.

(56) References Cited

U.S. PATENT DOCUMENTS

| | | | |
|---|---|---|---|
| 6,539,809 B1* | 4/2003 | Weiss | G01N 3/08 73/825 |
| 2007/0006850 A1* | 1/2007 | Ricco | F02M 55/025 123/456 |
| 2012/0061599 A1* | 3/2012 | Keizer | F16K 31/0672 29/401.1 |
| 2018/0224364 A1* | 8/2018 | Eversole | B65G 57/10 |
| 2019/0001765 A1* | 1/2019 | Jordan | B60C 23/04 |

FOREIGN PATENT DOCUMENTS

| | | | |
|---|---|---|---|
| CN | 108548716 | * | 9/2018 |
| EP | 1043579 A1 | | 10/2000 |

OTHER PUBLICATIONS

PCT, International Preliminary Report on Patentability regarding Application No. PCT/US2022/013267, dated Jul. 20, 2023 (9 pages).

* cited by examiner

*Primary Examiner* — Brandi N Hopkins
*Assistant Examiner* — Nigel H Plumb
(74) *Attorney, Agent, or Firm* — McAndrews, Held & Malloy, Ltd.

(57) ABSTRACT

Described is a compression apparatus for a testing system having a load cell. The disclosed compression apparatus ensures proper seating relative to the load cell to yield accurate compression friction (CF) measurements. The disclosed compression apparatus includes a compression rod and at least one mechanical fastener. The compression rod has a first portion at a distal end and a second portion that defines a threaded bore at a proximal end. The first portion is configured to contact a specimen and the second portion is configured to couple to the load cell. The mechanical fastener is configured to mate with the threaded bore.

21 Claims, 10 Drawing Sheets

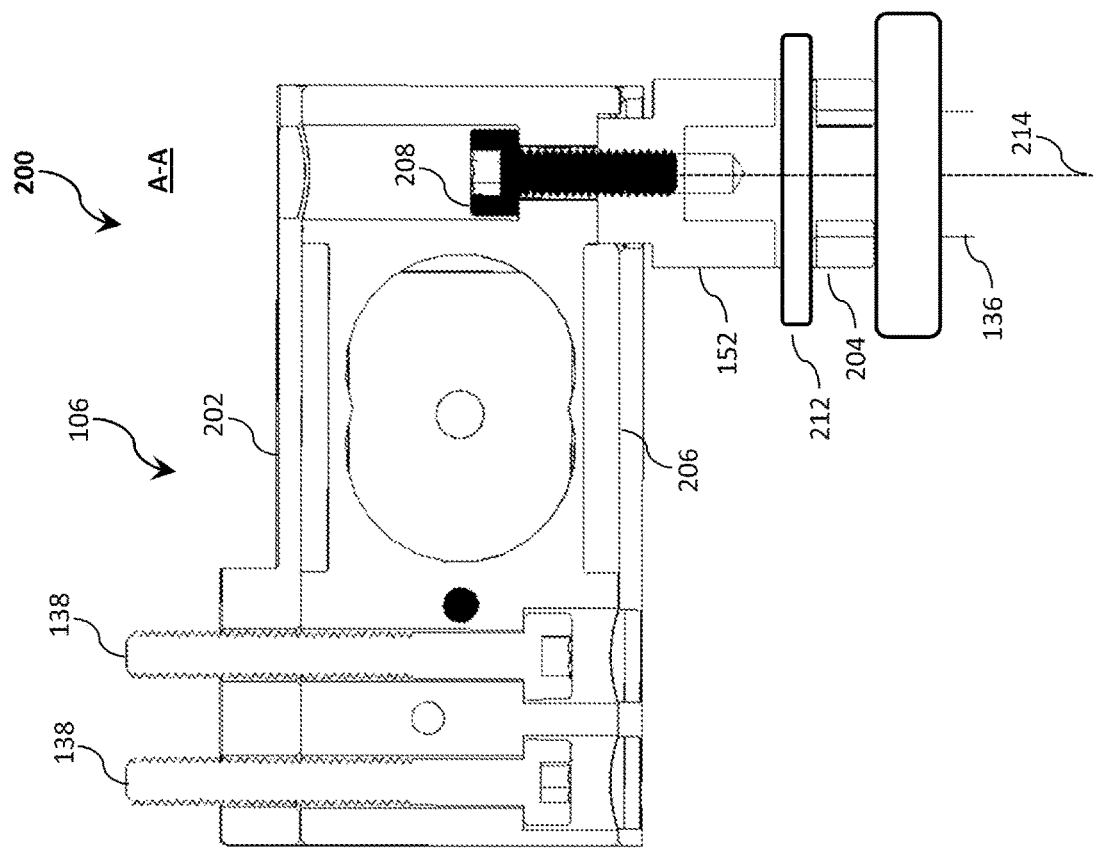
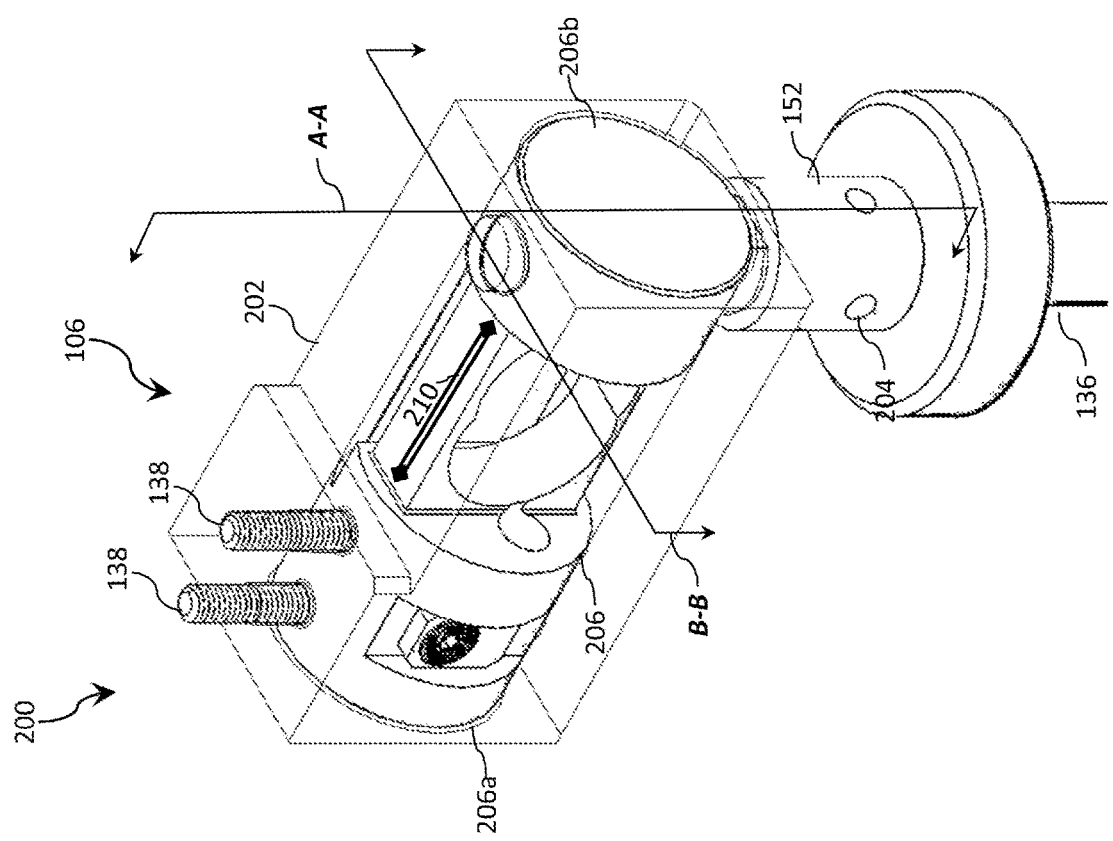
FIG. 2b
FIG. 2a

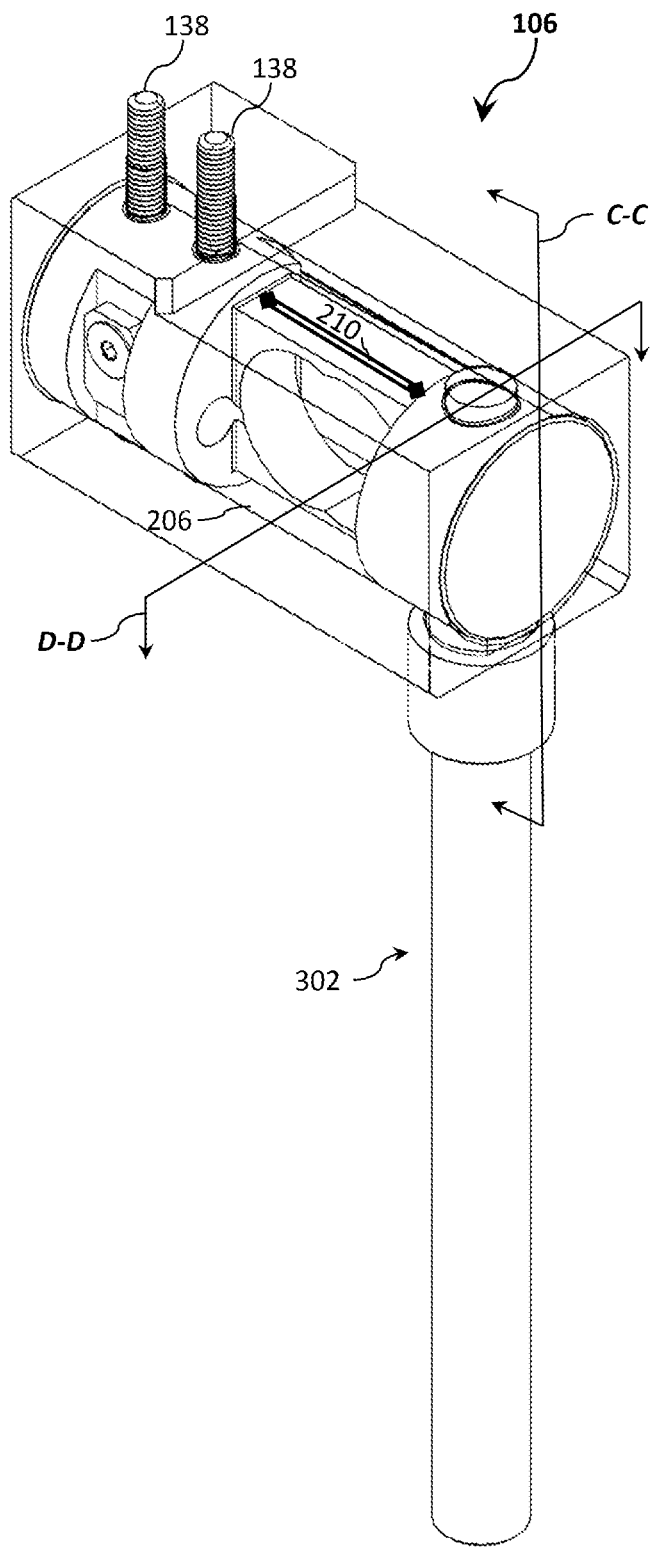 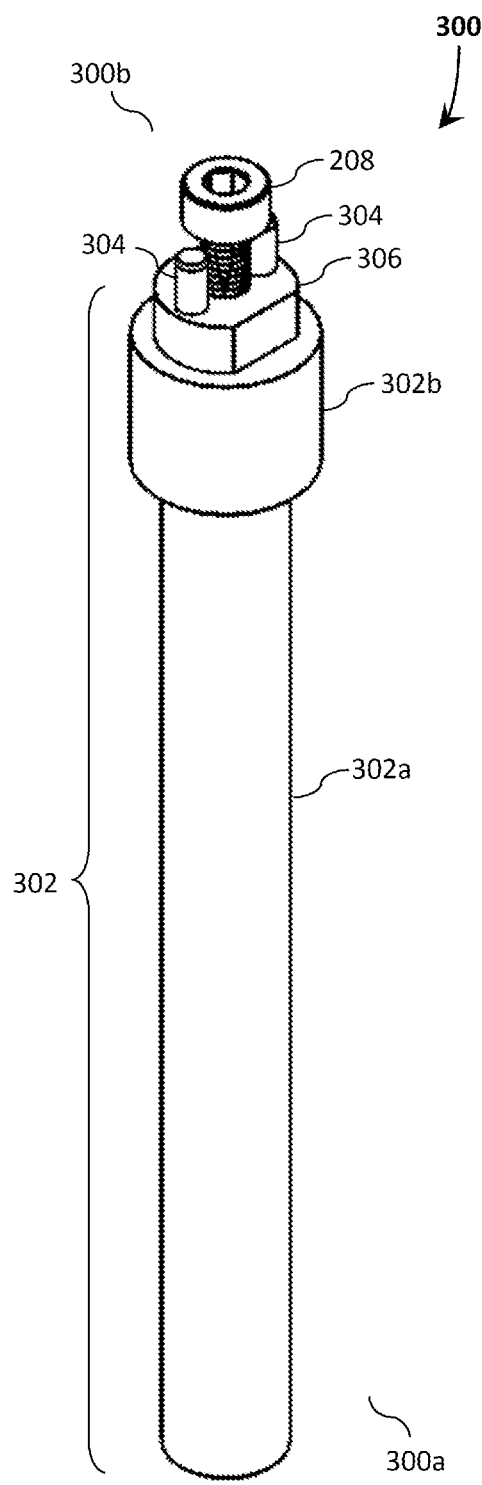
FIG. 3a     FIG. 3b

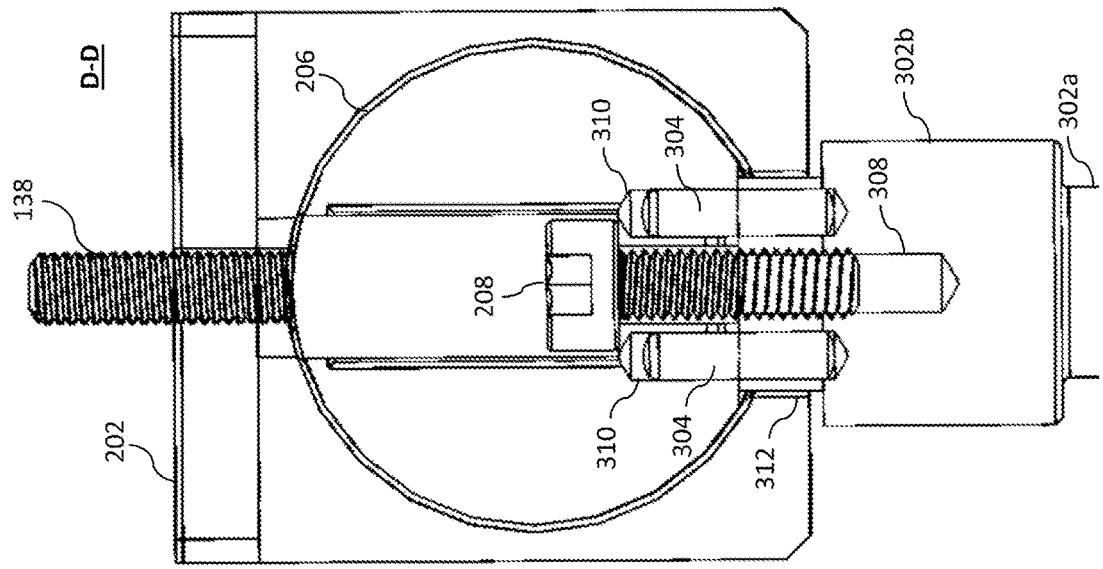
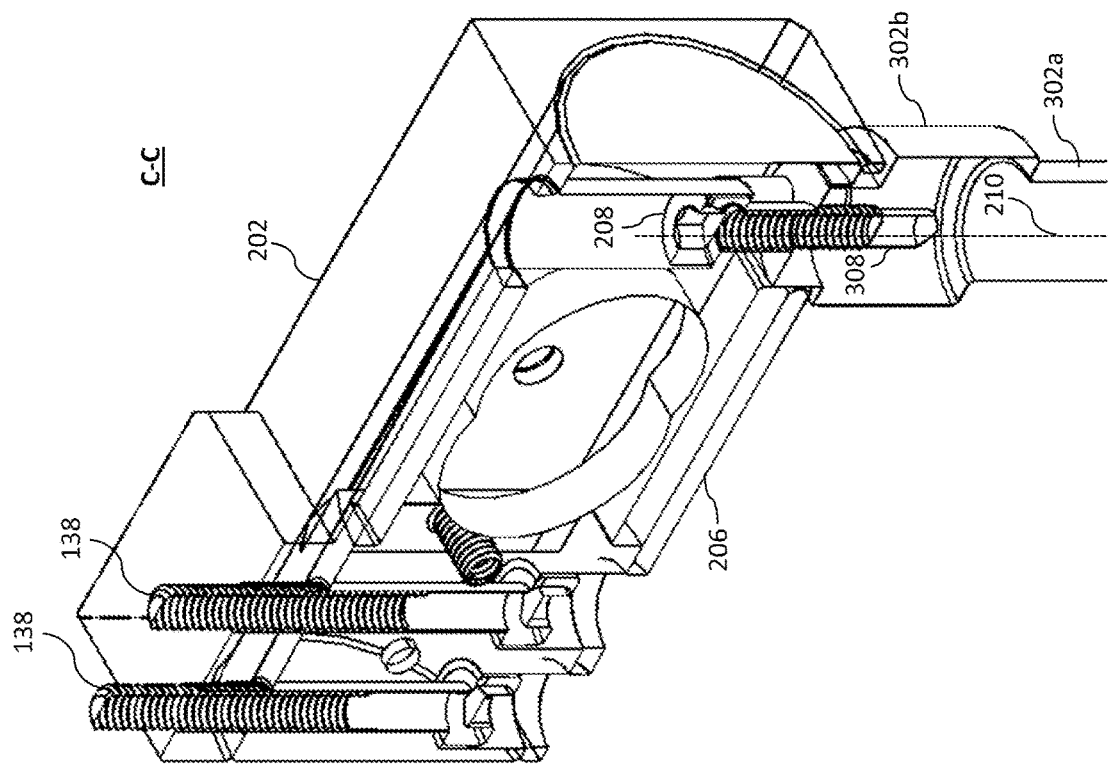
FIG. 3d
FIG. 3c

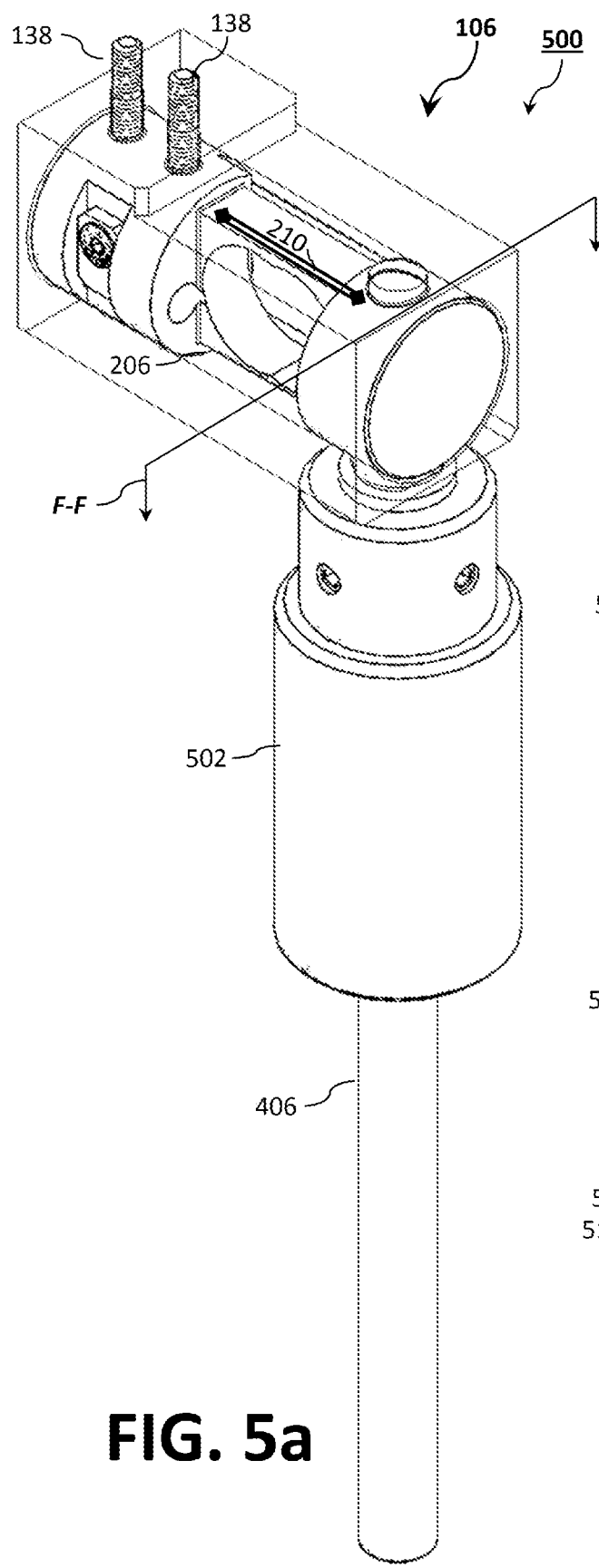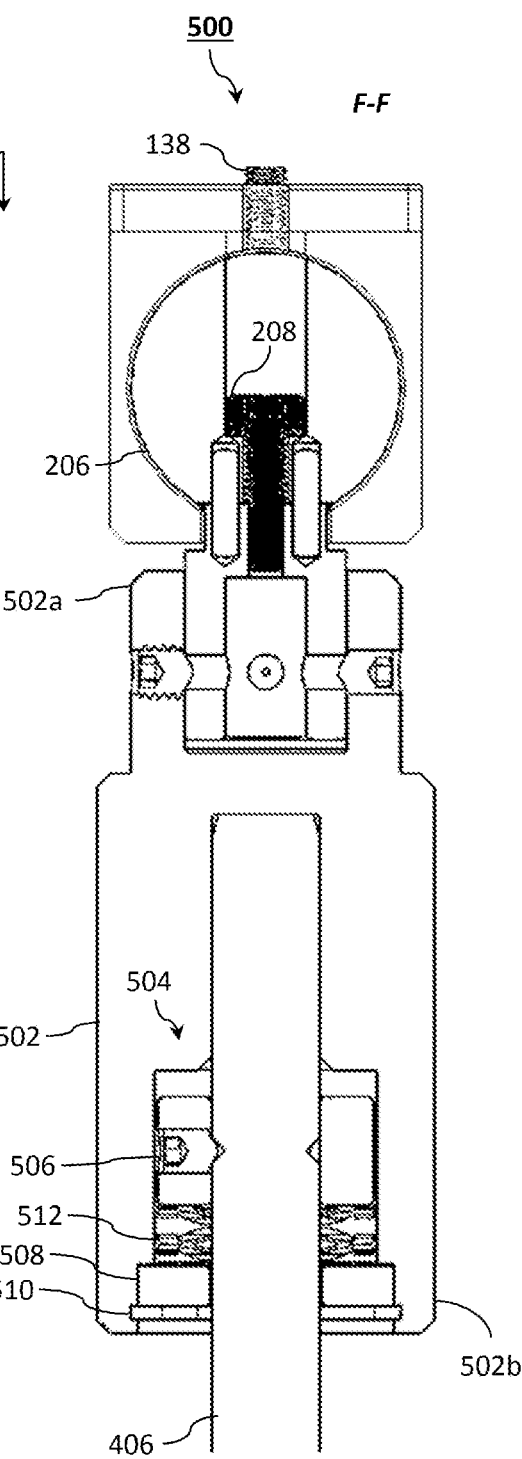
FIG. 5a  FIG. 5b

COMPRESSION APPARATUS FOR AUTOMATING SPECIMEN TESTING

CROSS REFERENCE TO RELATED APPLICATIONS

The present application claims the benefit of, and priority to, U.S. Provisional Patent Application No. 63/140,061, entitled "System, Method, And Apparatus For Automating Specimen Testing," filed Jan. 21, 2021, the entire contents of which are hereby incorporated by reference.

FIELD

The present disclosure is directed to specimen testing and, more particularly, to a system, method, and apparatus for automating residual seal force testing and/or compression friction measurement testing.

BACKGROUND

Since the early part of the 20$^{th}$ century, containers (e.g., cartridges, bottles, vials, etc.) with elastomeric closures and, in some cases, crimped caps have been a primary packaging system for parenteral (i.e., injectable) medicines. Parenteral products contained in such container package systems require a robust seal at the interface between the glass container and the elastomeric stopper to prevent contamination and product leakage. While the seal is established in the manufacturing process, it must withstand a variety of handling, processing, and storage conditions prior to use.

In some examples, container seal is composed of three major components—the glass container, an elastomeric closure (e.g., a rubber stopper), and a cap that secures the rubber stopper in the container, such as an aluminum cap. When a metal cap is used, typically an aluminum or aluminum alloy, the cap must be crimped onto the stopped container with a compressive force that will ensure sufficient mating of the container and elastomeric closure. In other examples, the cap is removed for other testing. Closure variables that affect the container seals include dimensional characteristics and tolerances, along with the mechanical properties of the closure components, including modulus, hardness, and compression set.

Manufacturers of parenteral containers are required to employ a quantitative method for measuring the force a closure exerts against the container after the initial seal is made and throughout the shelf life of the product. In the case of a closure that uses a metal cap, this force measured using a residual seal force ("RSF") test, while a compression friction ("CF") measurement test is used evaluate a glass container that is sealed using a plunger. A CF measurement test is sometimes called a glide test. While existing RSF and CF testers can measure the RSF and CF, such testing can be time consuming, tedious, and labor intensive. Therefore, it is desirable to provide a more accurate, more tolerant, and/or automated system, method, and apparatus for RSF and/or CF testing.

SUMMARY

Systems, methods, and apparatuses for testing are disclosed, substantially as illustrated by and described in connection with at least one of the figures. More particularly, systems, methods, and apparatuses are disclosed for determining the residual seal force and/or compression friction measurement for containers, particularly containers for parenteral pharmaceutical products.

BRIEF DESCRIPTION OF THE DRAWINGS

The foregoing and other objects, features, and advantages of the devices, systems, and methods described herein will be apparent from the following description of particular embodiments thereof, as illustrated in the accompanying figures; where like or similar reference numbers refer to like or similar structures. The figures are not necessarily to scale, emphasis instead being placed upon illustrating the principles of the devices, systems, and methods described herein.

FIG. 2a illustrates a perspective view of a first example load cell in accordance with aspects of this disclosure.

FIG. 2b illustrates a plan cross-sectional view of the first example load cell taken along section A-A of FIG. 2a.

FIG. 2c illustrates a plan cross-sectional view of the first example load cell taken along section B-B of FIG. 2a.

FIG. 3a illustrates a perspective view of a second example load cell in accordance with aspects of this disclosure.

FIG. 3b illustrates a perspective view of the compression apparatus in accordance with aspects of this disclosure.

FIG. 3c illustrates a plan cross-sectional view of the second example load cell taken along section C-C of FIG. 3a.

FIG. 3d illustrates a plan cross-sectional view of the second example load cell taken along section D-D of FIG. 3a.

FIG. 4b illustrates a plan cross-sectional view of the third example load cell taken along section E-E of FIG. 4a.

FIG. 5a illustrates a perspective view of a fourth example load cell in accordance with aspects of this disclosure.

FIG. 5b illustrates a plan cross-sectional view of the fourth example load cell taken along section F-F of FIG. 5a.

FIG. 6b illustrates a plan cross-sectional view of the fifth example load cell taken along section G-G of FIG. 6a.

DETAILED DESCRIPTION

Figure 1A:
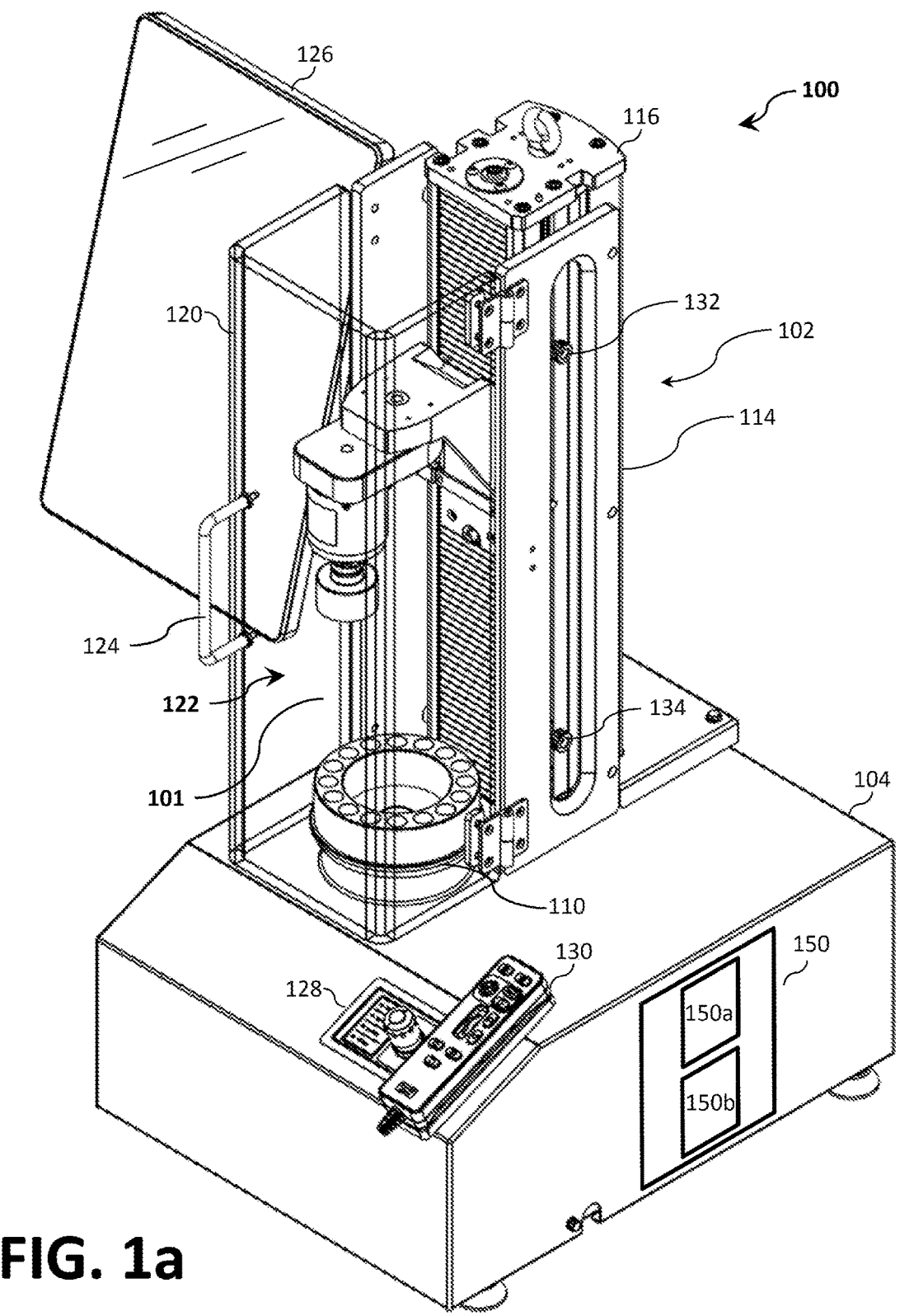
FIG. 1a illustrates a perspective view of an example testing system in accordance with aspects of this disclosure.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Recitation of ranges of values herein are not intended to be limiting, referring instead individually to any and all values falling within the range, unless otherwise indicated herein, and each separate value within such a range is incorporated into the specification as if it were individually recited herein. In the following description, it is understood that terms such as "first," "second," "top," "bottom," "side," "front," "back," and the like are words of convenience and are not to be construed as limiting terms. For example, while in some examples a first side is located adjacent or near a second side, the terms "first side" and "second side" do not imply any specific order in which the sides are ordered.

As used herein, the terms "about," "approximately," "substantially," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. The terms "e.g.," and "for example" set off lists of one or more non-limiting examples, instances, or illustrations. No language in the specification should be construed as indicating any unclaimed element as essential to the practice of the embodiments.

As used herein, the term "and/or" means any one or more of the items in the list joined by "and/or." As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y, and/or z" means "one or more of x, y, and z."

As used herein, the terms "circuit" and "circuitry" includes any analog and/or digital components, power and/or control elements, such as a microprocessor, digital signal processor (DSP), software, and the like, discrete and/or integrated components, or portions and/or combinations thereof.

As used herein, the terms "compression rod" and "compression pin" as used herein, each mean a rigid structure configured to impart a compressive force upon a specimen positioned in a testing system. In the case of a CF test, for example, the compression pin can be used to compress the elastomeric closure within a rigidly-supported parenteral container, such as a vial.

As used herein, the terms "drivingly coupled," "drivingly coupled to," and "drivingly coupled with" as used herein, each mean a mechanical connection that enables a driving part, device, apparatus, or component to transfer a mechanical force to a driven part, device, apparatus, or component.

As used herein, the term "processor" means processing devices, apparatuses, programs, circuits, components, systems, and subsystems, whether implemented in hardware, tangibly embodied software, or both, and whether or not it is programmable. The term "processor" as used herein includes, but is not limited to, one or more computing devices, hardwired circuits, signal-modifying devices and systems, devices and machines for controlling systems, central processing units, programmable devices and systems, field-programmable gate arrays, application-specific integrated circuits, systems on a chip, systems comprising discrete elements and/or circuits, state machines, virtual machines, data processors, processing facilities, and combinations of any of the foregoing. The processor may be, for example, any type of general purpose microprocessor or microcontroller, a digital signal processing (DSP) processor, an application-specific integrated circuit (ASIC). The processor may be coupled to, or integrated with a memory device.

As used herein, the term "memory" and/or "memory device" means computer hardware or circuitry to store information for use by a processor and/or other digital device. The memory and/or memory device can be any suitable type of computer memory or any other type of electronic storage medium, such as, for example, read-only memory (ROM), random access memory (RAM), cache memory, compact disc read-only memory (CDROM), electro-optical memory, magneto-optical memory, programmable read-only memory (PROM), erasable programmable read-only memory (EPROM), electrically-erasable programmable read-only memory (EEPROM), flash memory, solid state storage, a computer-readable medium, or the like.

A quantitative method for measuring a closure force exerted against a container after sealing can be performed using a constant rate of compression testing machine. By exerting a slow, constant rate of compression on a sealed container, a stress vs. time curve can be generated to determine a residual seal force (RSF) measurement of a given closure seal in a specimen. The RSF measurement can be determined for a variety of containers with various closure sizes and shapes. RSF measurements, for example, can be used to indicate the security of the container's closure as part of a manufacturer's quality control. The initial force with which the closure compresses the container is a function of the vertical and horizontal crimping forces applied during application (e.g., crimping) of the aluminum cap; however, due to the viscoelastic relaxation behavior of rubber, the force of the closure pressing against the containers decays as a function of time, elastomer composition, and as a result of various processing procedures. In another example, a compression friction (CF) measurement test can be performed using the compression testing machine to qualify a glass container that is sealed using an elastomeric closure (e.g., a plunger). A CF measurement test is sometimes referred to as a glide test.

To evaluate a seal tightness, manufacturers sometimes use manual testing systems as part of their quality control processes to measure the RSF or the CF of a parenteral package created during a container-sealing process. Typically, manufacturers test small batches or volumes (e.g., lot or line samples) as part of its quality control efforts. Because RSF and CF testing is considered destructive testing (i.e., the product is no longer saleable), manufacturers may test only between 0.5% and 1.25% of the production, or about 0.66% of the production. Further, operators, who are already busy with other production-related tasks, are only permitted a limited amount of time to perform each test (e.g., about 1-2 minutes per specimen). Automating the RSF and the CF testing processes, however, can increase the testing speed and the volume of product that can be tested. To automate RSF and CF testing, precautions must be taken to ensure that the specimen are properly loaded to the testing system to ensure accurate measurements.

Figure 1B:
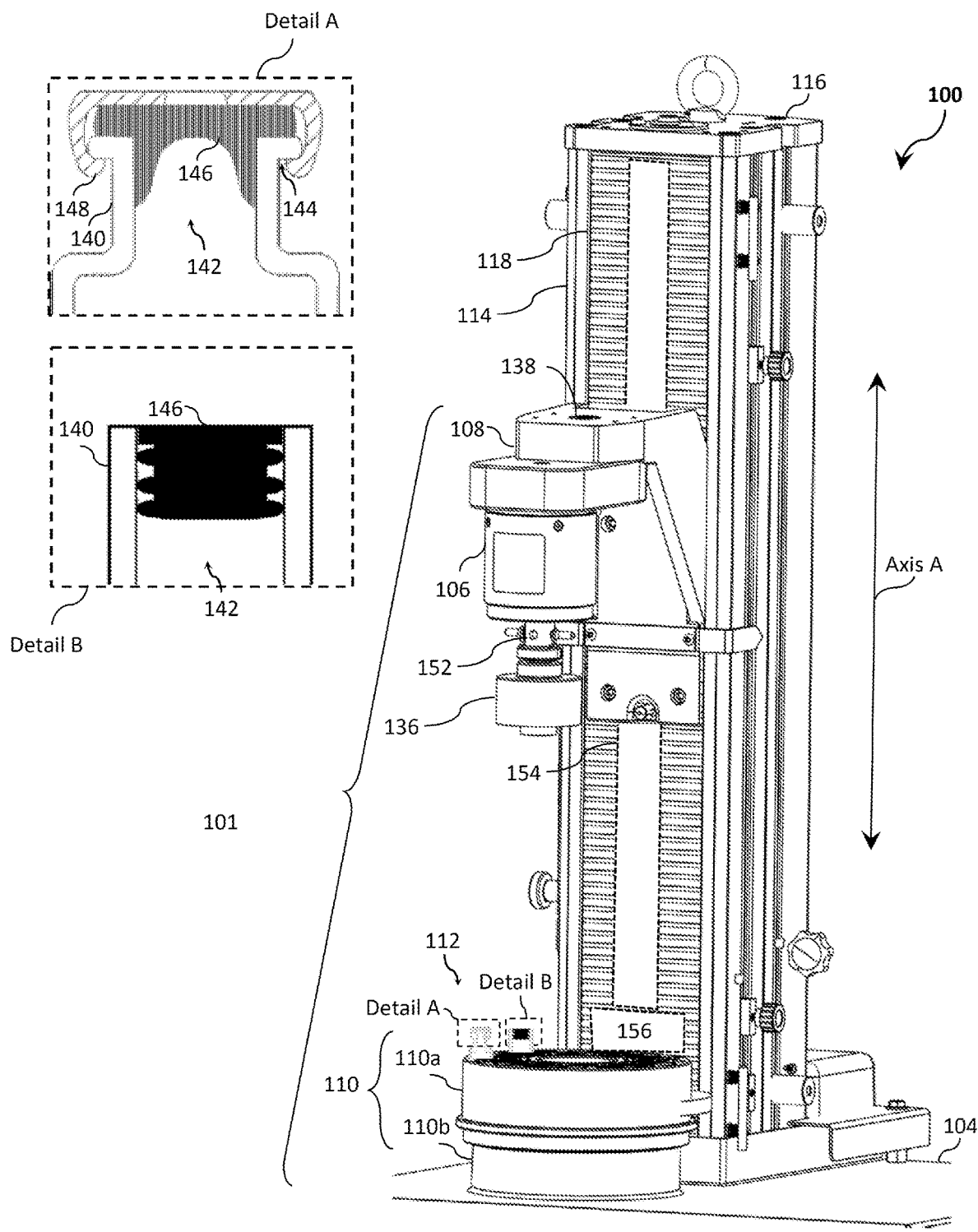
FIG. 1b illustrates a perspective view of the example testing system of FIG. 1a with portions removed to better illustrate the load string.

FIG. 1a illustrates perspective view of an example testing system 100, while FIG. 1b illustrates a perspective view of the load frame 102 of the example testing system 100 with portions omitted for clarity. The testing system 100 generally comprises a load frame 102, a load cell 106 mounted to a crosshead 108 of the load frame 102, a platen assembly 110 at a base structure 104 of the load frame 102, and a controller 150. As will be discussed, the platen assembly 110 is configured to support one or more specimens 112 during compression testing (e.g., RSF or CF testing), whether through a manual or automated process.

As best illustrated in FIG. 1a, the load frame 102 comprises a base structure 104, one or more columns 114, a moving crosshead 108, and a top plate 116. The load frame 102 serves as a high stiffness support structure against which the test forces react (e.g., compressive forces) during a test (e.g., a RSF test, compression friction measurement test, etc.). While the load frame 102 may be composed of a single column 114, as illustrated, multiple columns 114 may be employed, for example, in a dual column arrangement. The base structure 104 generally serves to support the one or more columns 114 and a platen assembly 110 that supports the specimen 112, while also housing various circuitry and components, such as a controller 150.

The platen assembly 110 may be manually or automatically adjusted (or otherwise controlled) to move or transfer a specimen 112 to a testing position, which is typically aligned below the test head 136, test apparatus, or other test accessory. The specimen 112 may be, for example, a container 140 for a parenteral pharmaceutical product as illustrated in FIG. 1b. As best illustrated in Detail A of FIG. 1b, in one example, the container 140 (e.g., a bottle with a flange 144) defines an opening 142 and a flange 144. An elastomeric closure 146 covers the opening 142. A cap 148 is crimped under flange 144 and compresses the elastomeric closure 146 to seal the opening 142. In another example, as best illustrated in Detail B of FIG. 1b, the cap 148 may be omitted whereby the elastomeric closure 146 fits within the opening 142 of the container 140 (e.g., a vial) and presses against the inner surface of the container 140 to seal the opening 142. While the specimen 112 is illustrated as a container 140 with and without a flange 144 and/or cap 148, other types of specimens 112 are also contemplated.

Each of the one or more columns 114 comprises a guide column and a ballscrew 154 that is drivingly coupled to an actuator 156. A ballscrew 154 is a form of mechanical linear actuator that translates rotational motion (e.g., from an actuator 156, such as a motor) to linear motion with little friction. In one example, the ballscrew 154 may include a threaded shaft that provides a helical raceway for ball bearings, which acts as a precision screw. As illustrated in FIG. 1b, the ballscrew 154 is housed within the one or more columns 114 between the base structure 104 and the top plate 116. The actuator 156 that drives the ballscrew 154 is controlled via the controller 150. A column cover 118 may be provided to protect the ballscrew 154 from dirt, grime, and damage, while also protecting the user from harm during operation. The testing system 100 comprises various sensors to monitor its operation. For example, the testing system 100 may include an upper limit switch 132 and a lower limit switch 134 to prevent the crosshead 108 from deviating from an acceptable range of motion along axis A. Upon triggering the upper limit switch 132 or the lower limit switch 134, the controller 150 may stop (or reverse) the actuator 156 to prevent damage to the testing system 100 or the specimen 112.

The crosshead 108 is mounted to both the guide column and the ballscrew 154 and supports the load cell 106. The ballscrew 154 is driven (e.g., rotated) via an actuator 156. Rotation of the ballscrew 154 drives the crosshead 108 up (away) or down (toward) relative to the base structure 104, while the guide column provides stability to the crosshead 108. The load cell 106 may be removably coupled to the crosshead 108 via one or more mechanical fasteners 138 (e.g., screws, bolts, socket head cap screws, etc.) to enable the operator to exchange the load cell 106 when desired. For example, the load cell 106 may become damaged, a different type of load cell 106 may be desired or needed, which can vary by test (e.g., RSF and CF testing).

The display device 126 (e.g., a touch screen display), control panel 128, and/or remote control 130 (e.g., a handset) may be used by the operator to monitor and/or control operation of the testing system 100. In some example, the control panel 128 and the remote control 130 may each provide one or more switches, buttons, or dials to control or adjust operation of the testing system 100 (e.g., an emergency stop button). The control panel 128 and the remote control 130 may further provide one or more status indicators (e.g., LEDs, lights, etc.) to provide a status of the testing system 100. The remote control 130 may be wired or wireless.

To provide additional protection and increase safety, the load string 101 may be housed in an enclosure 120 that defines a test chamber 122. The enclosure 120 may be fabricated from a transparent material (e.g., glass, plastic, Plexiglas, etc.) to enable the operator to observe the load string 101. A door or access panel 124 may be provided to enable access to the test chamber 122 within the enclosure 120. The load string 101 generally refers to the components installed between the moving crosshead 108 and the base structure 104 (or, where applicable, a fixed lower crosshead). Typically, the load string 101 includes the load cell 106, the test head 136, any adapters required to connect the components, and the specimen(s) 112 to be tested. Typically, for RSF testing, the load cell 106 is mounted on the crosshead 108, a test head 136 with an anvil is mounted to the load cell 106, and a specimen 112 is positioned on the base structure 104 (e.g., using a platen assembly 110). Similarly, for CF testing, a load cell 106 is mounted on the crosshead 108, a compression rod is mounted to the load cell 106, and a specimen 112 is positioned on the base structure 104 (e.g., using a platen assembly 110).

Operation of the testing system 100 may be automatically controlled and/or monitored via the controller 150. The controller 150 may comprise a processor 150a and memory device 150b configured with executable instructions. The controller 150 is operably coupled to, and configured to control, the various actuators (e.g., the actuator 156 that drives the ballscrew 154), sensors (e.g., load cell(s) 106, upper and lower limit switches 132, 134), user interfaces (e.g., display device 126, control panel 128, and/or remote control 130), etc.

During the RSF test, for example, the crosshead 108 moves down along Axis A of the load frame 102 (toward the base structure 104) to apply compressive load to the specimen 112 via a test head 136, test apparatus, or other test accessory that is coupled to the load cell 106. The test head 136 may be, or include, an anvil (also known as a dorn) configured to contact and compress the one or more specimens 112. The test head 136, test apparatus, or other test accessory may be coupled directly to a coupler 152 of the load cell 106 or via a compression rod or pin.

The load cell 106 converts this load into an electrical signal that the testing system 100 measures via controller 150 and displays to the operator via display device 126. In one example, the test head 136 may advance at a constant speed (e.g., about 0.01 inches/second). In other words, in this example, for every 0.001 inches the crosshead 108 travels along the column 114 (along Axis A), the controller 150 automatically records the force exerted by the specimen 112 in response to the movement (strain) imposed upon the specimen 112 by the test head 136. The constant speed may be adjusted for a given specimen 112. The controller 150 also automatically records the corresponding strain data. The resulting data set comprises a sequence of stress-strain measurements that can be graphed, which approximates a curve of predictable shape. In the case of RSF, an adequate seal may be determined by monitoring for an inflection point on resulting curve (e.g., indicating the elastomeric closure 146 has transitioned from flexing to rigid, thus sealing the opening 142).

The test head 136 may be designed for RSF and/or CF testing. For example, the test head 136 may be a compression rod for CF testing or include an anvil for RSF testing, such as a test head with an adjustable, conforming anvil. As can be appreciated, certain tests may warrant a specific type of test head 136. For example, the test head 136 used during RSF measurement may include an anvil that is sized and shaped to correspond to the size and shape of the closure of a parenteral container. Therefore, while the test head 136 is generally illustrated in FIGS. 1*a* and 1*b* as being configured for RSF testing, a compression rod (and associated load cell) may instead be used for CF testing.

The test head 136 can be interchangeable to enable the testing system 100 to be used for various types of tests (e.g., RSF, CF, tensile, compression, flexure, etc.). In other words, the test head 136 may be configured to removably couple with the load cell 106 via, for example, a coupler 152 or other means to enable the operator to replace or interchange the test head 136 with another the test head 136, test apparatus, or other test accessory. The coupler 152 may employ one or more of a collar coupling (e.g., a collar with one or more set pins or screws), clevis coupling, sleeve coupling, or a screw on coupling (e.g., a threaded rod). Therefore, while the coupler 152 is illustrated as a female collar coupler with set screws and/or set pins, other types of couplings are contemplated.

The one or more specimens 112 are supported on the base structure 104 by the platen assembly 110. Akin to the test head 136, certain tests may warrant a specific type of platen assembly 110. For example, the platen assembly 110 used during RSF measurement may include one or more stations that are sized and shaped to correspond to the size and shape of the parenteral container 140 (or other specimen 112). That that end, the platen assembly 110 may comprise an specimen plate 110*a* that is test specific or specimen specific, and a base plate 110*b* supported by the base structure 104 and configured to support the specimen plate 110*a*. The specimen plate 110*a* may be removably coupled to the base plate 110*b* to enable the operator to select a specimen plate 110*a* that is suitable for a particular test. In one example, the specimen plate 110*a* is a plate or table that is sized and shaped to support the one or more specimens 112 (e.g., via one or more recesses), while the base plate 110*b* may be a plate configured to support and/or secure the specimen plate 110*a* relative to the base structure 104. In some examples, the specimen plate 110*a* is configured to move relative to the base plate 110*b*. For example, the specimen plate 110*a* may be configured to rotate or tilt relative to the base plate 110*b* to accommodate an approach angle of the test head 136 during compression.

To yield accurate CF measurements, it is important that the test head 136 (e.g., a compressive rod, in the case of CF testing) firmly contacts the specimen 112 (e.g., the elastomeric closure 146) during a CF test. This typically requires that the operator check to ensure that the test head 136 is properly seated relative to the load cell 106 such that the flat surface of the elastomeric closure 146 is flush with the contact point of the test head 136. This particularly relevant when the test head 136 is not configured to conform to the position of the specimen 112, as is the case with compression rods. In an automated approach, this introduces additional complications.

Figure 2C:
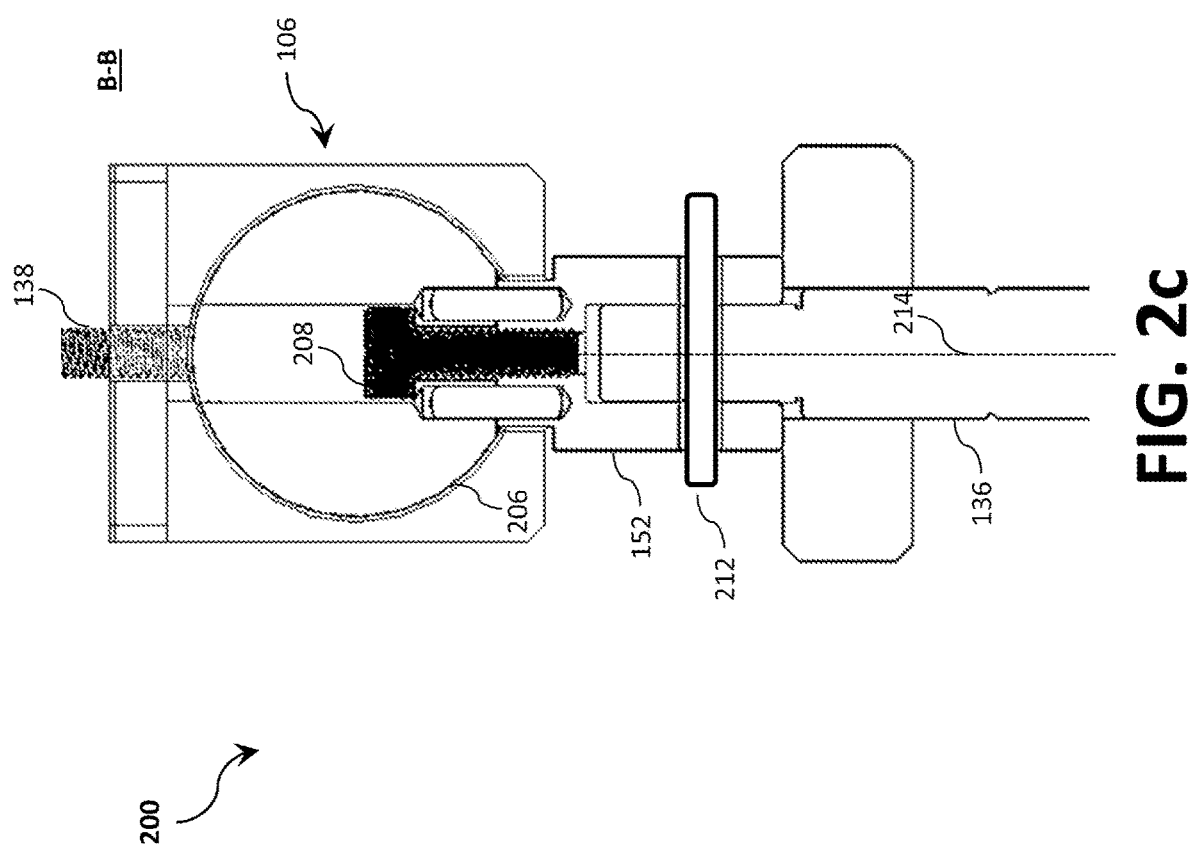

FIG. 2*a* illustrates a perspective view of a first example load cell assembly 200 in accordance with aspects of this disclosure, while FIGS. 2*b* and 2*c* illustrate, respectively, plan cross-sectional views of the first example load cell assembly taken along sections A-A and B-B of FIG. 2*a*. The load cell 106 is configured to convert a compression force into an electrical signal. In one example, the load cell 106 comprises an elastic member 206 and one or more strain gauges 210 coupled to the elastic member 206. The elastic member 206 may be a cylindrical-shaped elastic member and/or fabricated from a metal or a metal alloy.

As illustrated, the elastic member 206 comprises a proximal end 206*a* and distal end 206*b*. The proximal end 206*a* may be coupled to the crosshead 108 via one or more mechanical fasteners 138. The proximal end 206*a* may be coupled to the test head 136 via a coupler 152 and one or more mechanical fasteners 208. For example, the test head 136 may be inserted into the collar of the coupler 152 and secured by passing one or more pins or screws 212 through holes 204 and into the test head 136 to secure the test head 136 in place. The operator must use care to ensure that the one or more pins or screws 212 are inserted and/or tightened evenly. For example, overtightening one pin or screw 212 can push the test head 136 off of the center axis 214, resulting in a crooked test head 136. In other words, the longitudinal axis of the test head 136 should remain aligned with its direction of travel to ensure proper contact is achieved with the specimen 112. Therefore, while the coupler 152 allows for the test head 136 to be readily interchanged, it can introduce errors if not properly secured. To mitigate the risk, the coupler 152 may be omitted and a compression apparatus with an integrated coupling may be used.

FIG. 3*a* illustrates a perspective view of a second example load cell assembly in accordance with aspects of this disclosure, while FIG. 3*b* illustrates a perspective view of the compression apparatus 300. FIG. 3*c* and FIG. 3*d* illustrate, respectively, plan cross-sectional view of the second example load cell assembly taken along sections C-C and D-D of FIG. 3*a*.

The compression apparatus 300 comprises a compression rod 302 and a mechanical fastener 208. As illustrated, the compression rod 302 includes a first portion 302*a* at a distal end 300*a* and a second portion 302*b* that defines a threaded bore 308 at a proximal end 300*b*. The first portion 302*a* is configured to contact a specimen 112 and the second portion 302*b* is configured to couple to the load cell 106. The at least one mechanical fastener 208 is configured to couple the compression rod 302 to the elastic member 206 via the threaded bore 308.

The elastic member 206 comprises a proximal end 206*a* and distal end 206*b*. The proximal end is configured to attach to a crosshead 108 of the testing system 100 via one or more mechanical fasteners 138. The second portion 302*b* of the compression rod 302 is coupled to the distal end 206*b* via the mechanical fastener 208.

The first portion 302*a* and the second portion 302*b* are each cylindrical in shape. In some examples, the first portion 302*a* has a first diameter that is less than a second diameter of the second portion 302*b*. While the first portion 302*a* and the second portion 302*b* are illustrated as fabricated as a unitary structure, the first portion 302*a* and the second portion 302*b* may be separate components are permanently attached to one another (e.g., via welding or glue). The compression rod 302 may be fabricated as a unitary structure through die casting, computer numerical control (CNC) machining, lathe machining, 3D printing, etc.

The second portion 302*b* may further comprises one or more alignment features 304, 306. The one or more alignment features 304, 306 may include, for example a set of dowels 304 configured to mate with a corresponding set of recesses 310 of the load cell 106 and/or a clipped cylindrical protrusion 306 configured to slip into a corresponding clipped cylindrical recess 312 of the load cell 106. In some examples, the one or more alignment features 304, 306 and the second portion 302b are fabricated as a unitary structure. In other examples, the one or more alignment features 304, 306 and the second portion 302b are fabricated as separate structures. For example, the set of dowels 304 may be attached to the second portion 302b via a press-fit attachment, adhesive, threads, etc.

Figure 4A:
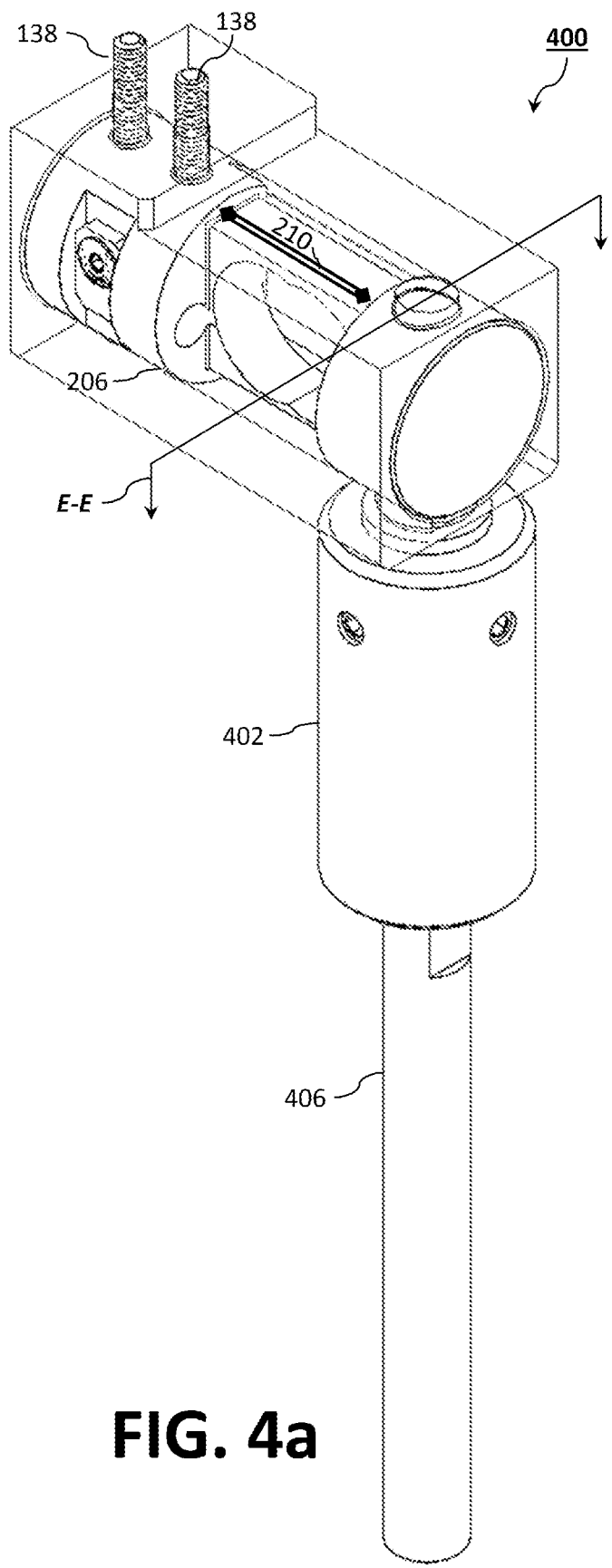
FIG. 4a illustrates a perspective view of a third example load cell in accordance with aspects of this disclosure.
Figure 4B:
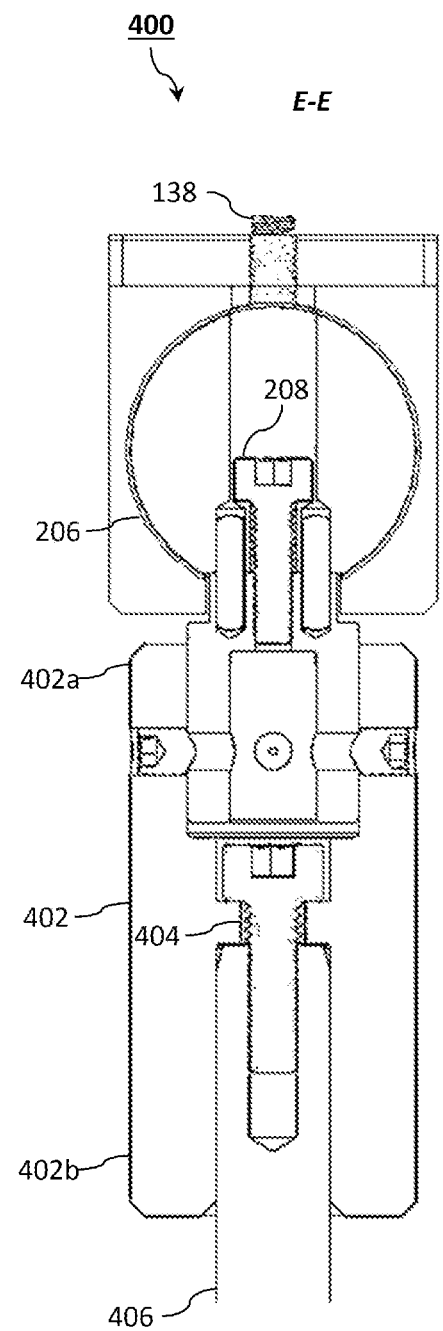

FIG. 4a illustrates a perspective view of a third example load cell 400 in accordance with aspects of this disclosure, while FIG. 4b illustrates a plan cross-sectional view of the third example load cell 400 taken along section E-E of FIG. 4a. In this example, the compression rod 406 is attached to the distal end 206b of the elastic member 206 via an adapter coupling 402. The proximal end 402a of the adapter coupling 402 couples to the elastic member 206 via, for example, a clevis much in the same way as the above-described coupler 152. The compression rod 406 is fastened to the distal end 402b of the adapter coupling 402 using, for example, one or more mechanical fasteners 404. To enable access to the head end of the one or more mechanical fasteners 404, the compression rod 406 can be attached to adapter coupling 402 before the adapter coupling 402 is attached to the clevis.

FIG. 5a illustrates a perspective view of a fourth example load cell 500 in accordance with aspects of this disclosure, while FIG. 5b illustrates a plan cross-sectional view of the fourth example load cell 500 taken along section F-F of FIG. 5a. In this example, the, compression rod 406 is attached to the distal end 206b of the elastic member 206 via an adapter coupling 502 having a spring assembly 504. The proximal end 502a of the adapter coupling 502 couples to the elastic member 206 via, for example, a clevis much in the same way as the above-described coupler 152. The compression rod 406 is fastened to the distal end 502b of the adapter coupling 502 using, for example, the spring assembly 504. The spring assembly 504 generally comprises a set screw coupling 506, retainer 508, snap ring 510, and wave spring 512. The set screw coupling 506 may be a set screw style shaft collar with 3 set screws at 120 degrees apart and configure to engage the groove (e.g., a V-groove) in the compression rod 406. The wave spring 512 biases the compression rod 406 against the adapter coupling 502 to ensure that there is no compliance in a compression application.

Figure 6A:
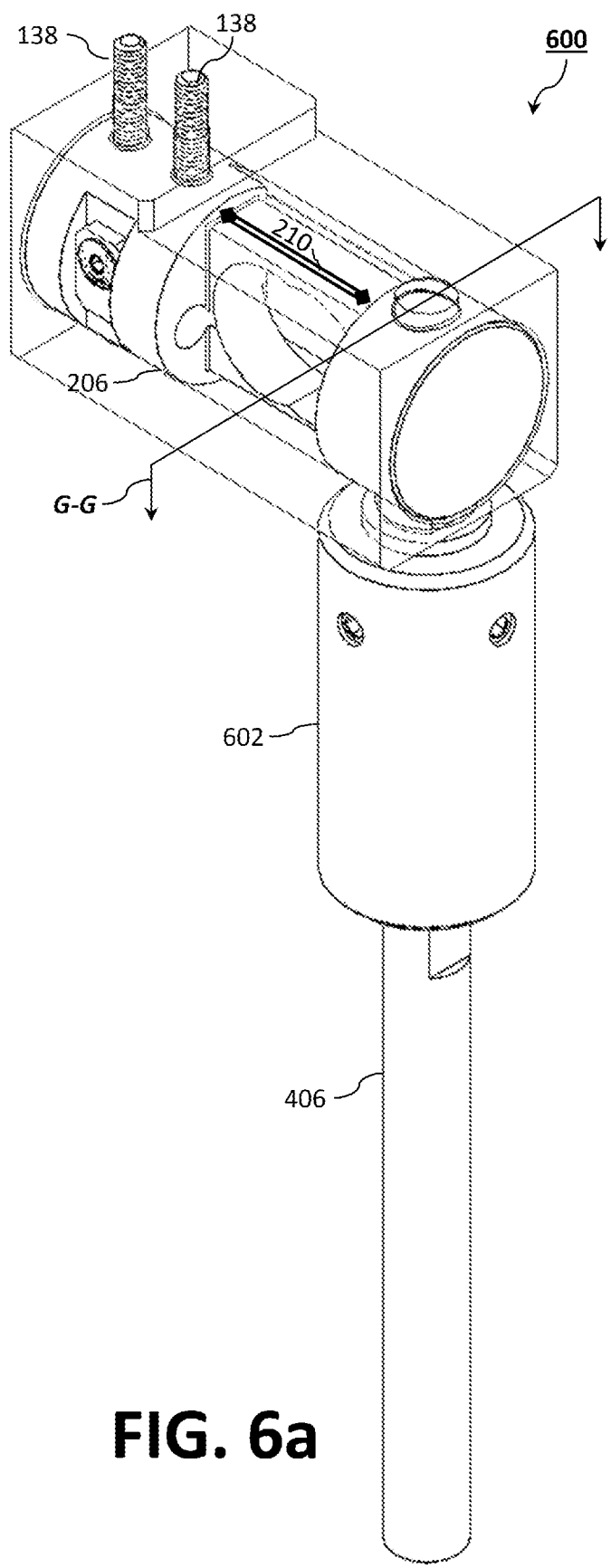
FIG. 6a illustrates a perspective view of a fifth example load cell in accordance with aspects of this disclosure.
Figure 6B:
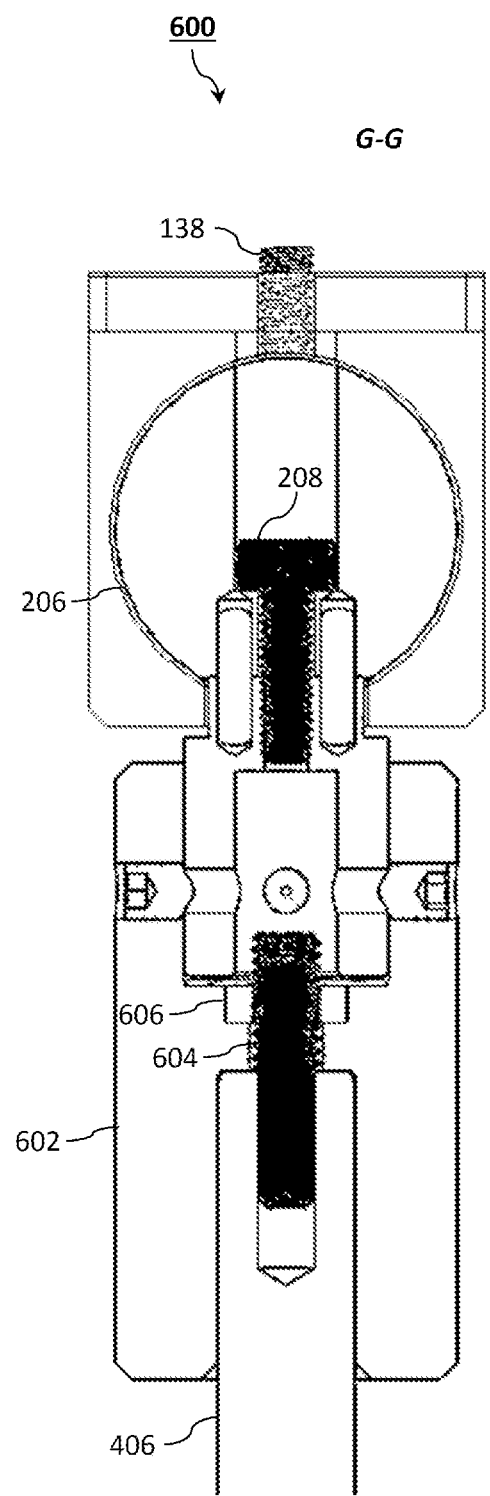

FIG. 6a illustrates a perspective view of a fifth example load cell 600 in accordance with aspects of this disclosure, while FIG. 6b illustrates a plan cross-sectional view of the fifth example load cell 600 taken along section G-G of FIG. 6a. In this example, the compression rod 406 is attached to the distal end 206b of the elastic member 206 via an adapter coupling 602. The proximal end 602a of the adapter coupling 602 couples to the elastic member 206 via, for example, a clevis much in the same way as the above-described coupler 152. The compression rod 406 is fastened to the distal end 602b of the adapter coupling 602 using, for example, one or more mechanical fasteners. In this example, the one or more mechanical fasteners include a threaded rod 604 and a nut 606 (e.g., a square nut). To enable access to the head end of the one or more mechanical fasteners 404, the compression rod 406 can be attached to adapter coupling 402 before the adapter coupling 402 is attached to the clevis.

Figure 7:
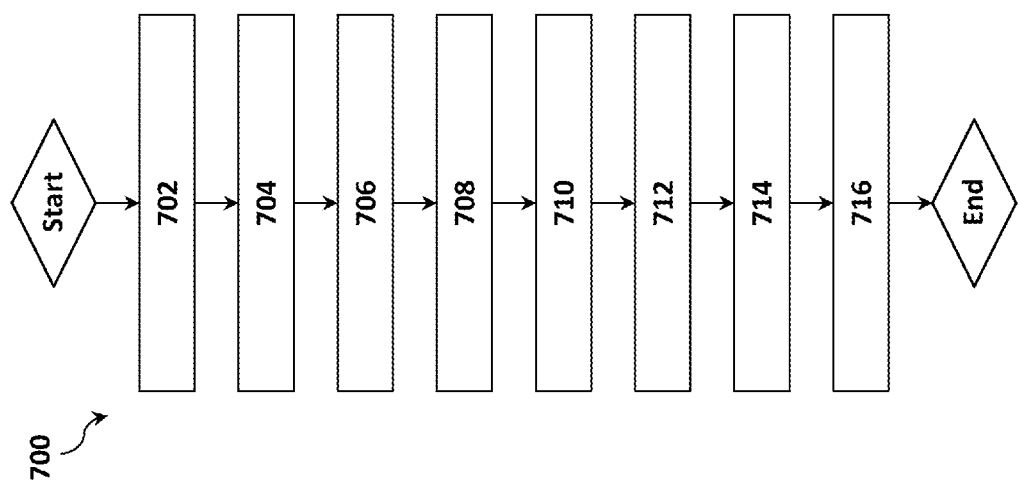
FIG. 7 is a flowchart representative of an example method for operating the example testing system.

FIG. 7 is a flowchart representative of an example method 700 for performing an automated compression friction test in a testing system 100. While a compression friction test is described, RSF measurements can similarly be taken via testing system 100. The testing system 100 comprises a load cell 106 configured to move along a column 114 toward and away from a base structure 104 via a crosshead 108.

At step 702, a plurality of specimens 112 are loaded to a specimen plate 110a. The plurality of specimens 112 are loaded to a specimen plate 110a may be loaded through a manual or automated process. The plurality of specimens 112 comprises a first specimen 112 and a subsequent specimen 112 (e.g., a second specimen 112).

At step 704, the specimen plate 110a is positioned in a first position that situates the first specimen 112 at a testing position of the testing system 100. The specimen plate 110a can be positioned in a first position manually (e.g., by the operator before the test is commenced) or via an actuator.

At step 706, the actuator 156 advances the crosshead 108 along the column 114 toward the base structure 104 to compress the first specimen 112.

At step 708, the processor 150a, which is operatively coupled to the load cell 106, determines a compression friction measurement of the first specimen 112.

At step 710, the actuator 156 retracts the crosshead 108 along the column 114 away the base structure 104.

At step 712, the specimen plate 110a is moved in a second position that situates the subsequent specimen 112 at the testing position.

At step 714, the actuator 156 advances the crosshead 108 along the column 114 toward the base structure 104 to compress the subsequent specimen 112.

At step 716, the processor 150a determines a compression friction measurement of the subsequent specimen 112.

Steps 712 through 716 may be automatically repeated for each subsequent specimen 112 until each of the plurality of specimens 112 loaded to the specimen plate 110a is tested.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. For example, block and/or components of disclosed examples may be combined, divided, re-arranged, and/or otherwise modified. Therefore, the present method and/or system are not limited to the particular implementations disclosed. Instead, the present method and/or system will include all implementations falling within the scope of the appended claims, both literally and under the doctrine of equivalents.

What is claimed is:

1. A compression apparatus for a testing system having a load cell, the compression apparatus comprising:
    a compression rod having a first portion at a distal end and a second portion that defines a threaded bore at a proximal end, wherein the first portion is configured to contact a specimen and the second portion is configured to couple to the load cell; and
    a mechanical fastener configured to mate with the threaded bore.

2. The compression apparatus of claim 1, wherein the first portion and the second portion are each cylindrical in shape.

3. The compression apparatus of claim 2, wherein the first portion has a first diameter that is less than a second diameter of the second portion.

4. The compression apparatus of claim 1, wherein the first portion and the second portion are fabricated as a unitary structure.

5. The compression apparatus of claim 1, wherein the first portion and the second portion are permanently attached to one another.

6. The compression apparatus of claim 1, wherein the second portion further comprises one or more alignment features.

7. The compression apparatus of claim 6, wherein the one or more alignment features comprises a set of dowels configured to mate with a corresponding set of recesses of the load cell.

8. The compression apparatus of claim 7, wherein the set of dowels are attached to the second portion via threads.

9. The compression apparatus of claim 7, wherein the set of dowels and the second portion are fabricated as a unitary structure.

10. The compression apparatus of claim 7, wherein the one or more alignment features comprises a clipped cylindrical protrusion configured to slip into a corresponding clipped cylindrical recess of the load cell.

11. The compression apparatus of claim 10, wherein the clipped cylindrical protrusion and the second portion are fabricated as a unitary structure.

12. A test apparatus for a testing system, the test apparatus comprising:
    a load cell configured to convert a compression force into an electrical signal, wherein the load cell comprises an elastic member and one or more strain gauges coupled to the elastic member;
    a compression rod having a first portion at a distal end and a second portion at a proximal end that defines a threaded bore, wherein the first portion is configured to contact a specimen and the second portion is configured to couple to the elastic member; and
    a mechanical fastener configured to couple the compression rod to the elastic member via the threaded bore.

13. The test apparatus of claim 12, wherein elastic member comprises a proximal end and distal end, wherein the second portion of the compression rod is coupled to the distal end via the mechanical fastener.

14. The test apparatus of claim 13, wherein the proximal end is configured to attach to a crosshead of the testing system via one or more mechanical fasteners.

15. The test apparatus of claim 12, wherein elastic member is a cylindrical-shaped elastic member.

16. The test apparatus of claim 12, wherein the elastic member is fabricated from a metal or a metal alloy.

17. The test apparatus of claim 12, wherein the second portion further comprises one or more alignment features.

18. The test apparatus of claim 17, wherein the one or more alignment features comprises a set of dowels configured to mate with a corresponding set of recesses formed at the distal end of the elastic member.

19. The test apparatus of claim 18, wherein the one or more alignment features comprises a clipped cylindrical protrusion configured to slip into a corresponding clipped cylindrical recess formed at the distal end of the elastic member.

20. The test apparatus of claim 19, wherein the clipped cylindrical protrusion and the second portion are fabricated as a unitary structure.

21. The test apparatus of claim 12, wherein the first portion and the second portion are each cylindrical in shape, wherein the first portion has a first diameter that is less than a second diameter of the second portion.

* * * * *